United States Patent [19]

Nanba et al.

[11] Patent Number: 4,690,784
[45] Date of Patent: Sep. 1, 1987

[54] PROCESS FOR PREPARING PHOSPHATIDYLCHOLINE DERIVATIVES

[75] Inventors: Yukihiro Nanba; Toshiyuki Sakakibara, both of Kobe, Japan

[73] Assignee: Nippon Fine Chemical Co., Ltd., Osaka, Japan

[21] Appl. No.: 738,220

[22] Filed: May 28, 1985

[30] Foreign Application Priority Data

May 30, 1984 [JP] Japan ................... 59-110450

[51] Int. Cl.$^4$ .............................................. C07F 9/10
[52] U.S. Cl. .................................. 260/403; 558/169
[58] Field of Search ................ 260/403, 925; 558/169

[56] References Cited

PUBLICATIONS

Robles et al., *Biochimica et Biophysica Acta*, 187, (1969), 520-526.
Baer et al., *Canadian Journal of Biochemistry and Physiology*, vol. 37, (1959), 953-959.
*Journal of Lipid Research*, 20, (1979), 674-677, authored by K. M. Patel et al.
*Journal of the American Chemical Society*, 87, (1965), 5522-5523, authored by Y. Laipdot et al.
*Chemistry and Physics of Lipids*, 22, (1978), 293-305, authored by J. G. Lammers et al.
*Journal of Lipid Research*, 18, (1977), 548, authored by T. G. Warner et al.

*Primary Examiner*—Charles F. Warren
*Assistant Examiner*—Elizabeth A. Hanley
*Attorney, Agent, or Firm*—Armstrong, Nikaido, Marmelstein & Kubovcik

[57] ABSTRACT

This invention provides a process for preparing a phosphatidylcholine derivative represented by the formula

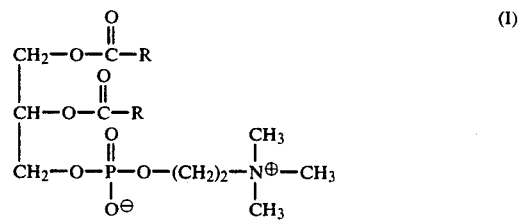

wherein R represents straight- or branched-chain and-saturated or unsaturated hydrocarbon group, the process comprising the steps of (i) providing a suspension or solution of glycerophosphatidylcholine and a carrier in a solvent and removing the solvent from the suspension or solution by distillation to obtain a powder, and (ii) reacting the glycerophosphatidylcholine present in the powder with an acid anhydride or acid halide in a solvent and in the presence of a basic catalyst to acylate the glycerophosphatidylcholine.

15 Claims, No Drawings

PROCESS FOR PREPARING PHOSPHATIDYLCHOLINE DERIVATIVES

This invention relates to a process for preparing phosphatidylcholine derivatives and more particularly to a process for preparing phosphatidylcholine derivatives represented by the formula

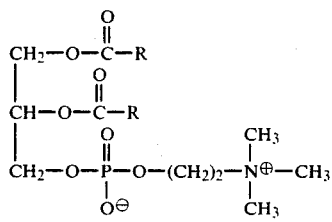

wherein R represents straight- or branched-chain and saturated or unsaturated hydrocarbon group.

The phosphatidylcholine derivatives of the formula (I) have a variety of physiological actions and are therefore useful as pharmaceuticals. For example, dipalmitoyl phosphatidylcholine exhibits a surface activity in the lung and thus can be used as a drug for ameliorating the respiratory function (Akino, "Aburakagaku (Oil Chemistry)," 30, 705 (1981), and Kobayashi et al., "Nihon Kaimen Igakukai Zassi (J. of Jap. Med. Soc. Biol. Interface)", 14, 59 (1983)); dilinoleoyl phosphatidylcholine is useful for treating lipometabolic disorder in the liver, cholesteremia and arteriosclerosis ("Saikin no Shin Yaku (New Drugs in Japan)," Vol. 20, page 179); and dieicosapentaenoyl phosphatidylcholine can significantly inhibit the platelet aggregation (Kito, "Seikagaku," Vol. 56, No. 8, page 597). Further the derivatives of the formula (I) can be used as a material for preparing liposome and thus are useful as a material for preparing pharmaceuticals (Haga, "Kagaku no Ryoiki (Journal of Japanese Chemistry)," 36, 248 (1982) and Hidaka et al., "Yuki Gosei Kagaku Kyokai Shi (Journal of Synthetic Organic Chemistry, Japan)," 40, 377 (1982)) and also are usable as a cosmetic material. Because of their surface-activity and functions in biological membranes in addition, extensive researches on the derivatives of the formula (I) are being carried out.

Various processes are known for preparing phosphatidylcholine derivatives. However, conventional processes have drawbacks and are not fully satisfactory. For example, it is known to prepare the derivatives of the formula (I) by acylating a cadmiunm chloride complex of glycerophosphatidylcholine with an acid anhydride in a solvent and in the presence of 4-pyrrolidinopyridine and removing the cadmium chloride and 4-pyrrolidinopyridine (Kanu M. Patel et al., J. Lipid. Res. 20, 674 (1979)). This process poses the serious problems that the cadmium chloride extremely harmful to the living body remains in the final product and that even purification by ion-exchange chromatography and like means can not completely remove the remaining cadmium chloride from the final product. Therefore, even the purified product contains several ppm of cadmium chloride. Accordingly the product prepared by this process can not be used for pharmaceuticals, cosmetics and the like.

A process is also known which comprises the steps of dissolving glycerophosphatidylcholine and potassium salt of stearic acid in methanol, evaporating the solution to dryness to obtain a powder and bringing the powder into contact with stearic anhydride in the absence of a solvent to give the derivative of the formula (I) (E. Cubero Robles et al., Biochem. Biophys. Acta. 187 (1969), 520–526). This process, however, gives a large amount of by-product having the phosphate group migrated to the 2-position. This by-product is usually separated by column chromatography, but with very low separation efficiency. Therefore the process produces a final product in yields of as low as about 50%. See also J. G. Lammers, Chemistry and Physics of Lipids, 22 (1978) 293–305, especially 297–299. Furthermore, the yields resulting from the practice of the process widely vary depending on stirring conditions and thus the process is poor in reproducibility. With such defects, the process is not commerically advantageous.

Known processes for preparing the derivative of the formula (I) further include one which comprises reaction of glycerophosphatidylcholine and acylimidazole to permit acylation (J. G. Lammers, Chemistry and Physics of Lipids, 22 (1978) 293–305 and Warner et al., Lipid Res. 18, 1977, 548). This process also presents problems of giving a final product in unsatisfactory yields, failing to effectively produce a final product in which R is a saturated hydrocarbon group, taking long reaction time (more than 120 hours) and requiring the use of an expensive reactant such as acylimidazole. Therefore this process is not commercially satisfactory.

An object of the present invention is to provide a commercially advantageous process for preparing the phosphatidylcholine derivatives of the formula (I) without the foregoing drawbacks of conventional processes.

Another object of the invention is to provide a process for preparing the derivatives of the formula (I) in high yields.

A further object of the invention is to provide a process for preparing the derivatives of the formula (I) without using a harmful reactant such as cadmium chloride or an expensive reactant such as acylimidazole.

A still further object of the invention is to provide a process for preparing the derivatives of the formula (I) without involving the migration of phosphate group.

These objects and other features of the present invention will become more apparent from the following description.

This invention provides a process for preparing a phosphatidylcholine derivative represented by the formula

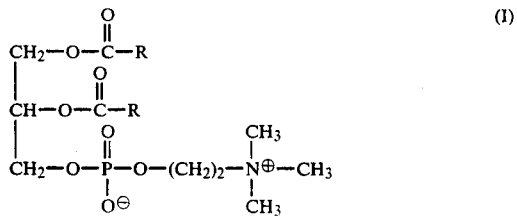

wherein R represents straight- or branched-chain and saturated or unsaturated hydrocarbon group, the process comprising the steps of:

(i) providing a suspension or solution of (a) glycerophosphatidylcholine represented by the formula

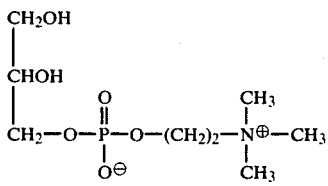

and (b) a carrier selected from the group consisting of porous mineral material, inorganic neutral salt, alkali metal salt of higher fatty acid and alkaline earth metal salt of higher fatty acid in a solvent and removing the solvent from the suspension or solution by distillation to obtain a powder, and (ii) reacting the glycerophosphatidylcholine of the formula (II) present in the powder with an acid anhydride represented by the formula $$(RCO)_2O \qquad (III)$$

wherein R is as defined above or an acid halide represented by the formula $$RCOX \qquad (IV)$$

wherein R is as defined above and X represents halogen atom such as chlorine, bromine and iodine in a solvent and in the presence of a basic catalyst to acylate the glycerophosphatidylcholine of the formula (II).

We conducted research to develop a commercially advantageous process for preparing phosphatidylcholine derivatives of the formula (I) without the drawbacks of conventional processes. We found that the desired phosphatidylcholine derivatives of the formula (I) can be reproducibly prepared with a great commercial advantage by preparing a suspension or solution containing the glycerophosphatidylcholine of the formula (II) and a specific carrier, evaporating the suspension or solution to dryness to obtain a powder and reacting the powder with the compound of the formula (III) or (IV) in a solvent and in the presence of a basic catalyst. The process of this invention generally gives the phosphatidylcholine derivatives of the formula (I) in high yields of about 75% or more. Since the process does not employ any harmful reactant such as cadmium chloride, the final product is free from such harmful substance and accordingly is usable for physiological purposes, e.g., as pharmaceuticals, cosmetics and the like. Because the present process involves no migration of phosphate group, the reaction product can be purified with extreme ease, affording a final compound of high purity. Moreover, the present process can produce the derivative of the formula (I) in the form of any of L-isomer, D-isomer and DL-isomer by selection of the starting compound (II).

The hydrocarbon group represented by R in the formula (I) according to this invention is not limited to particular kinds and can be any of straight- and branched-chain, and saturated and unsaturated groups. More specifically, useful hydrocarbon groups include straight- or branched-chain saturated aliphatic groups having 1 to 30 carbon atoms, preferably 6 to 24 carbon atoms, and straight- or branched-chain unsaturated aliphatic groups having 2 to 30 carbon atoms, preferably 6 to 24 carbon atoms, and containing 1 to 6 double bonds and/or 1 to 3 triple bonds. Typical of the saturated aliphatic hydrocarbon groups are those which, when taken together with carbonyl, form acyl group (RCO) such as acetyl, propionyl, butyryl, caproyl, 2-ethylhexanoyl, caprinoyl, lauroyl, myristoyl, palmitoyl, isostearoyl, stearoyl, docosanoyl, tetracosanoyl, hexacosanoyl, triacontanoyl, etc. Examples of the unsaturated hydrocarbons are those which, when taken together with carbonyl, form acyl group (RCO) such as myristoleoyl, palmitoleoyl, linoleoyl, oleoyl trans-9octadecenoyl, cis-13-dococenoyl, 9,12-octadecadienoyl, 9,12,15-octadecatrienoyl, 2,4-octadecadienoyl, eicosapentaenoyl, octadecadiynoyl, docosahexanoyl, adrenoyl, etc.

The process of this invention is carried out as follows. As a first step, the starting compound of the formula (II) and a specific type of carrier are suspended or dissolved in a solvent and the solvent is removed from the suspension or solution by evaporation. This step permits smooth progress of acylation in a second step to be described later. More specifically, the compound of the formula (II) is dissolved in a solvent. The amount of the solvent used is about 1 to about 100 times, preferably about 5 to about 50 times, the weight of the compound of the formula (II). To the solution is added a carrier. The amount of the carrier used is about 1 to about 100 times, preferably about 2 to about 30 times, the weight of the compound of the formula (II). Then the mixture is stirred to obtain a suspension or solution. The solvent is distilled off preferably under reduced pressure, and the residue is made into powder. Preferred examples of solvents are water and saturated aliphatic monohydric alcohols having 1 to 3 carbon atoms such as methanol, ethanol, propanol and isopropanol.

Examples of useful carriers are porous mineral materials, alkali metal salts or alkaline earth metal salts of higher fatty acids, and inorganic neutral salts.

Examples of porous mineral materials are zeolite, talc, terra alba, silica, alumina, kaolin, diatomaceous earth, montmorillonite, etc.

Useful alkali or alkaline earth metal salts of higher fatty acids include those which contain straight- or branched-chain and saturated or unsaturated hydrocarbon groups having 6 or more carbon atoms, preferably 6 to 30 carbon atoms. Specific examples thereof are salts of higher fatty acids such as caproic acid, caprylic acid, lauric acid, myristic acid, palmitic acid, stearic acid, behenic acid, myristoleic acid, palmitoleic acid, elaidic acid, erucic acid, oleic acid, arachic acid, lignoceric acid (tetracosanoic acid), cerotic acid (hexacosanoic acid), etc. Exemplary of alkali metals are sodium, potassium, lithium and the like. Representative of alkaline earth metals are calcium, magnesium, barium and the like. Alkali metal salts and alkaline earth metal salts of higher fatty acids are used as they are. Alternatively they may be formed in situ by adding the higher fatty acid and hydroxide of alkali metal or alkaline earth metal, preferably in equivalent ratio, to the solvent. Although it is preferred to use a higher fatty acid having a hydrocarbon group which is the same as that of acid anhydride of the formula (III) or acid halide of the formula (IV), also usable is a higher fatty acid with a hydrocarbon group different from that of the compound of the formula (III) or (IV). In the latter case, several percents of the compound of the formula (I) may contain the hydrocarbon group of the carrier, but such compounds can be easily separated.

Useful inorganic neutral salts include salts prepared from strong acid such as sulfuric acid, hydrochloric acid or the like and strong base such as hydroxide of alkali metal, hydroxide of alkaline earth metal or the like. Examples of such salts are magnesium sulfate, sodium sulfate, sodium chloride, calcium chloride, barium chloride, etc.

The carriers are usually used in the form of a powder except when the alkali or alkaline earth metal salts of higher fatty acids are formed in situ. The particle size of the carrier is not particularly limited. From a viewpoint of reaction efficiency, however, it is preferable to use a carrier having a particle size of not greater than 250 μm, more preferably about 1 to about 100 μm. If a carrier soluble in the solvent is used, it will dissolve therein completely or result in the reduction of the particle size upon dissolution. Accordingly such soluble carriers, when used, may have a particle size of larger than 250 μm.

In the step (ii) according to this invention, the powder obtained in the step (i) is suspended in a solvent and the compound of the formula (II) contained in the powder is acylated with acid anhydride of the formula (III) or acid halide of the formula (IV) in the presence of a basic catalyst, whereby the final compound of the formula (I) is produced.

The kinds of solvents usable in the step (ii) are not particularly limited and include halogenated hydrocarbons having 1 to 2 carbon atoms such as chloroform, methylchloroform, methylene chloride, ethylene dichloride and the like; aromatic hydrocarbons such as benzene, toluene, xylene, mesitylene and the like; saturated aliphatic hydrocarbons having 5 to 10 carbon atoms such as pentane, hexane, heptane, cyclohexane, octane, decane and the like; esters of fatty acid having 2 to 3 carbon atoms with saturated aliphatic monohydric alcohol having 1 to 3 carbon atoms such as ethyl acetate, propyl acetate, isopropyl acetate, methyl acetate, methyl propionate, ethyl propionate and the like; and ethers such as diethyl ether, tetrahydrofuran, diisopropyl ether and the like. The amount of the solvent used in the step (ii) is not particularly limited but generally ranges from about 3 to about 300 times the weight of the compound of the formula (II) used in the step (i).

Examples of the basic catalyst useful in the step (ii) are tertiary amines and pyridine derivatives represented by the formula

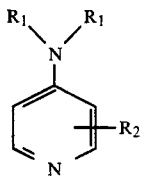 (V)

wherein $R_1$ represents straight- or branched-chain alkyl group having 1 to 4 carbon atoms or two $R_1$ groups, when taken together with the nitrogen atom to which they are attached, form pyrrolidino group and $R_2$ represents alkyl group having 1 to 4 carbon atoms or hydrogen atom. Examples of the pyridine derivatives of the formula (V) are N,N-dimethyl-4-aminopyridine, N,N-dimethyl-4-amino-2-methylpyridine, N,N-diethyl-4-aminopyridine, N,N-dibutyl-4-amino-3-ethylpyridine, 4-pyrrolidinopyridine, 4-pyrrolidino-2-isopropylpyridine, 4-pyrrolidino- 3-butyl-pyridine and the like. Of the compounds of the formula (V), those wherein $R_1$ is $C_1$-$C_4$ alkyl can be prepared by reacting 4-chloropyridine or $C_1$-$C_4$ alkyl substituted 4-chloropyridine with a di($C_1$-$C_4$alkyl)amine according to a method described in L. Pentimalli et al., Gazz. Chim. Ital., 94, 902 (1964).

The compounds of the fomula (V) wherein two $R_1$ groups, together with the nitrogen atom to which they are attached, form pyrrolidino group, can be prepared by reacting 4(1H)-pyridone or $C_1$-$_4$ alkyl substituted 4(1H)-pyridone with trimethylsilyl chloride, and reacting the resulting 4-trimethylsilyloxy-pyridine with pyrrolidine in the presence of $HgCl_2$, as described by H. Vorbüggen, Angew. Chem. internat. Ed., 11, 305 (1972). Examples of tertiary amines are tri($C_1$-$C_8$)-amines such as triethylamine, tributylamine, diisopropylethylamine, trioctylamine, tripropylamine, triisopropylamine and the like. The amount of the basic catalyst used generally ranges from about 0.01 to about 10 moles, preferably from about 0.1 to about 2 moles, per mole of the compound of the formula (II) used in the step (i).

The acid anhydride of the formula (III) or acid halide of the formula (IV) acts as an acylating agent to introduce the RCO group for the final compound of the formula (I). Therefore suitable acylating agents are those having any of the hydrocarbon groups as exemplified above for the substituent R in the formula (I). Examples of the acid anhydride of the formula (III) are acetic anhydride, propionic anhydride, butyric anhydride, caproic anhydride, 2-ethylhexanoic anhydride, capric anhydride, lauric anhydride, palmitic anhydride, isostearic anhydride, stearic anhydride, oleic anhydride, linoleic anhydride, linolenic anhydride, octadecadiynoic anhydride, 2,4-octadecadienoic anhydride, eicosapentaenoic anhydride, docosanoic anhydride, hexacosanoic anhydride, triacontanoic anhydride, myristic anhydride, myristoleic anhydride, palmitoleic anhydride, elaidic anhydride, erucic anhydride, arachic anhydride, lignoceric anhydride, cerotic anhydride, etc. Useful acid halides of the formula (IV) include chlorides, bromides, iodides or like halides of the acids constituting the anhydrides exemplified above. The amount of the acid anhydride of the formula (III) or acid halide of the formula (IV) used is in the range of about 1 to about 20 moles, preferably about 2 to about 10 moles, more preferably about 3 to about 5 moles, per mole of the compound of the formula (II) used in the step (i).

The acylation is carried out at a temperature of about 0° to about 100° C., preferably about 15° to about 45° C. and is completed in about 1 to about 100 hours, preferably about 12 to about 48 hours. The acylation may be carried out in air. However, it is preferred to conduct the acylation in an atmosphere of inert gas such as nitrogen, argon, helium and the like, especially when the hydrocarbon group of compound of the formula (III) or (IV) used is unsaturated.

After completion of the reaction, the desired compound can be easily separated from the reaction product by conventional separation and purification methods such as solvent extraction, recrystallization, various types of chromatography, etc.

In this way, the contemplated compound, i.e., phosphatidylcholine derivative of the formula (I), is prepared. The yield of the final compound, calculated on the basis of the entire reaction, is generally as high as about 75% or more.

This invention will be described below in more detail with reference to the following examples.

EXAMPLE 1

In 100 ml of methanol were dissolved 3 g (11.65 mM) of L-α-glycerophosphatidylcholine, 6 g (23.3 mM) of palmitic acid and 1.31 g (23.3 mM) of potassium hydroxide, and the solution was stirred. The methanol was distilled off by an evaporator and the residue was dried over $P_2O_5$ under reduced pressure and made into powder. The powder was placed in a 300 ml, 4-necked flask. To the reactor were further charged 11.6 g (23.3 mM) of palmitic anhydride, 1.7 g (11.65 mM) of 4-pyrrolidinopyridine and 100 ml of chloroform, and the mixture was stirred in an $N_2$ atmosphere at 40° C. for 48 hours. After completion of the reaction, 200 ml of chloroform was further added to the reaction mixture and the resulting mixture was left to stand in a refrigerator overnight. The precipitate was removed by filtration and the filtrate was washed twice with a 0.2 N aqueous solution of HCl containing a 50% aqueous solution of methanol and 4 times with a 50% aqueous solution of methanol. The filtrate was dried over magnesium sulfate and the chloroform was distilled off. The residue comprises L-$\beta,\gamma$-dipalmitoyl-$\alpha$-phosphatidylcholine, excess of the acid anhydride used, and the acid and small amounts of impurities formed during the reaction. The residue was purified by gradient elution on a silica gel column (eluent: chloroform-methanol mixture), giving 7.2 g of L-$\beta,\gamma$-dipalmitoyl-$\alpha$-phosphatidylcholine in a yield of 80%. M.p. 235° to 236° C. $[\alpha]_D^{20} = 6.7°$ (C=4.3 in a 1:1 mixture of chloroform and methanol). These values were identical with those already reported. The IR, NMR and TLC data were also identical with those already reported for the desired compound.

EXAMPLE 2

In 100 ml of methanol were dissolved 3 g of DL-$\alpha$-glycerophosphatidylcholine, 6 g of myristic acid and 1.31 g of potassium hydroxide and the solution was stirred. The methanol was distilled off by an evaporator and the residue was dried over $P_2O_5$ under reduced presure and made into powder. The powder was placed in a 300 ml, 4-necked flask. To the reactor were further charged 12 g of linoleic anhydride, 1.7 g of N,N-dimethyl-4-aminopyridine and 100 ml of methylchloroform. The mixture was stirred in an $N_2$ atmosphere at 30° C. for 48 hours. After completion of the reaction, 100 ml of methylchloroform was added to the reaction mixture and the resulting mixture was left to stand in a refrigerator overnight. The precipitate was removed by filtration and the filtrate was washed once with a 0.2 N aqueous solution of HCl containing a 50% aqueous solution of methanol and 4 times with a 50% aqueous solution of methanol. The filtrate was dried over magnesium sulfate and the methylchloroform was distilled off. The residue comprised DL-$\beta,\gamma$-dilinoleoyl-$\alpha$-phosphatidylcholine, excess of the acid anhydride used, and the acid and small amounts of impurities formed during the reaction. The residue was purified by gradient elution on a silica gel column (eluent: chloroformmethanol mixture), giving 7 g of DL-$\beta,\gamma$-dilinoleoyl-$\alpha$-phosphatidylcholine in a yield of 77%. The IR, NMR and TLC data were identical with those already reported for the desired compound.

EXAMPLE 3

A 3 g quantity of DL-$\alpha$-glycerophosphatidylcholine was dissolved in 100 ml of methanol. To the solution was added 8 g of diatomaceous earth (trademark "Celite," product of Manville Products Corp., United States, 10 $\mu$m or less in particle size) and the mixture was stirred. The methanol was distilled off by an evaporator and the residue was dried over $P_2O_5$ under reduced pressure and made into powder. The same subsequent procedure as in Example 2 was repeated, giving 7.1 g of DL-$\beta,\gamma$-dilinoleoyl-$\alpha$-phosphatidylcholine in a yield of 78%. The IR, NMR and TLC data were identical with those already reported for the desired compound.

EXAMPLE 4

A 3 g quantity of L-$\alpha$-glycerophosphatidylcholine was dissolved in 100 ml of methanol. To the solution was added 8 g of neutral alumina (15–40 $\mu$m in particle size) and the mixture was stirred. The methanol was distilled off by an evaporator and the residue was dried over $P_2O_5$ under reduced pressure and made into powder. The same subsequent procedure as in Example 1 was repeated, giving 7.0 g of L-$\beta,\gamma$-dipalmitoyl-$\alpha$-phosphatidylcholine in a yield of 77.7%. The final compound was found to have a melting point of 235° to 236° C., corresponding to the value already reported. The IR, NMR and TLC data were identical with those already reported for the desired compound.

EXAMPLE 5

A 3 g quantity of L-$\alpha$-glycerophosphatidylcholine was dissolved in 100 ml of methanol. To the solution was added 12 g of magnesium sulfate (10 $\mu$m or less in particle size) and the mixture was stirred. The methanol was distilled off by an evaporator and the residue was dried over $P_2O_5$ under reduced pressure and made into powder. The same subsequent procedure as in Example 1 was repeated, giving 6.8 g of L-$\beta,\gamma$-dipalmitoyl-$\alpha$-phosphatidylcholine in a yield of 75.4%. The final compound was found to have a melting point of 235° to 236° C., corresponding to the value already reported. The IR, NMR and TLC data were identical with those already reported for the desired compound.

EXAMPLE 6

A 3 g quantity of L-$\alpha$-glycerophosphatidylcholine was dissolved in 200 ml of methanol. To the solution was added 12 g of talc (10 $\mu$m or less in particle size) and the mixture was stirred. The methanol was distilled off by an evaporator and the residue was dried over $P_2O_5$ under reduced pressure and made into powder. The powder was placed into a 300 ml, 4-necked flask. Into the reactor were further charged 12 g of oleic anhydride, 2 g of N,N-diethylaminopyridine and 100 ml of methylene chloride. The mixture was stirred in an $N_2$ atmosphere at 40° C. for 24 hours. The same subsequent procedure as in Example 2 was repeated, giving 6.9 g of L-$\beta$, $\gamma$-dioleoyl-$\alpha$-phosphatidylcholine in a yield of 75%. The IR, NMR and TLC data were identical with those already reported for the desired compound.

EXAMPLE 7

A 3 g quantity of L-$\alpha$-glycerophosphatidylcholine was dissolved in 200 ml of methanol. To the solution was added 15 g of calcium chloride (50 $\mu$m or less in particle size) and the mixture was stirred. The methanol was distilled off by an evaporator and the residue was dried over $P_2O_5$ under reduced pressure and made into powder. The powder was placed into a 300 ml, 4-necked flask. To the reactor were further charged 12 g of oleic anhydride, 1 g of 4-pyrrolidinopyridine and 100 ml of chloroform. The mixture was stirred in an $N_2$ atmosphere at 40° C. for 24 hours. The same subsequent procedure as in Example 2 was repeated, giving 7 g of L-β,γ-dioleoyl-α-phosphatidylcholine in a yield of 76%. The IR, NMR and TLC data were identical with those already reported for the desired compound.

EXAMPLE 8

A 3 g quantity of L-α-glycerophosphatidylcholine was dissolved in 100 ml of methanol. To the solution was added 8 g of diatomaceous earth (trademark "Celite," product of Manville Products Corp., United States, 10 μm or less in particle size) and the mixture was stirred. The methanol was distilled off by an evaporator and the residue was dried over P₂O₅ under reduced pressure and made into powder. The powder was placed into a 300 ml, 4-necked flask. To the reactor were further charged 25.6 g (46.6 mmol) of stearic anhydride, 1 g (23.3 mmol) of triethylamine and 100 ml of chloroform. The mixture was stirred in an N₂ atmosphere at 45° C. for 48 hours. The same subsequent procedure as in Example 1 was repeated, giving 6.9 g of L-β,γ-distearoyl-α-phosphatidylcholine in a yield of 75.5%. The IR, NMR and TLC data were identical with those already reported for the desired compound.

We claim:

1. A process for preparing a phosphatidylcholine derivative represented by the formula

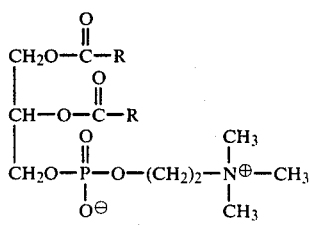

wherein R represents straight- or branched-chain and saturated or unsaturated hydrocarbon group, the process consisting essentially of the steps of:

(i) providing a suspension or solution of (a) glycerophosphatidylcholine represented by the formula

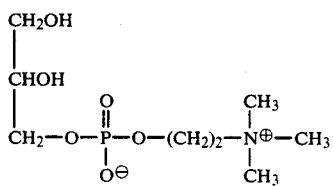

and (b) a carrier selected from the group consisting of a porous mineral material and an inorganic neutral salt in a solvent and removing the solvent from the suspension or solution by distillation to obtain a powder, and (ii) reacting the glycerophosphatidylcholine of the formula (II) present in the powder with an acid anhydride represented by the formula:

(RCO)₂O    (III)

wherein R is as defined above or an acid halide represented by the formula

RCOX    (IV)

wherein R is as defined above and X represents halogen atom, in a solvent and in the presence of a basic catalyst, to acylate the glycerophosphatidylcholine of the formula (II)

wherein the carrier is used in an amount of about 1 to about 100 parts by weight per part by weight of the gylcerophosphatidylcholine of the formula (II) and wherein the basic catalyst is tri(C₁-C₄alkyl)amine or a pyridine derivative represented by the formula

wherein R₁ represents straight- or branched-chain alkyl group having 1 to 4 carbon atoms or two R₁ groups, when taken together with the nitrogen to which they are attached, form a pyrrolidino group, and R₂ represents an alkyl group having 1 to 4 carbon atoms or an hydrogen atom.

2. A porocess as defined in claim 1 wherein the solvent in the step (i) is used in an amount of about 1 to about 100 parts by weight per part by weight of the glycerophosphatidylcholine of the formula (II).

3. A process as defined in claim 1 wherein the solvent in the step (i) is distilled off from the suspension or solution under reduced pressure.

4. A process as defined in claim 1 wherein the solvent in the step (ii) is used in an amount of about 3 to about 300 parts by weight per part by weight of the glycerophosphatidylcholine of the formula (II).

5. A process as defined in claim 1 wherein the basic catalyst is used in an amount of about 0.01 to about 10 moles per mole of the glycerophosphatidylcholine of the formula (II).

6. A process as defined in claim 1 wherein the acid anhydride of the formula (III) or acid halide of the formula (IV) is used in an amount of about 1 to about 20 moles per mole of the glycerophosphatidylcholine of the formula (II).

7. A process for preparing a phosphatidylcholine derivative represented by the formula

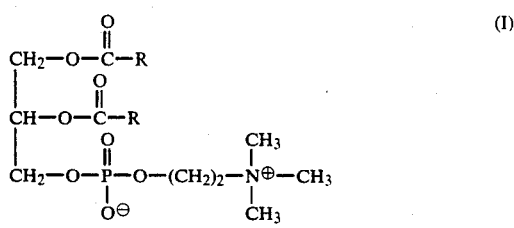

wherein R represents straight- or branched-chain and saturated or unsaturated hydrocarbon group, the process consisting essentially of the steps of (i) providing a suspension or solution of (a) 1 part by weight of glycerophosphatidylcholine represented by the formula

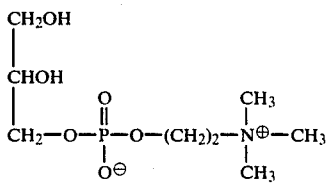

and (b) about 1 to about 100 parts by weight of a carrier selected from the group consisting of a porous mineral material and inorganic neutral salt in about 1 to about 100 parts by weight of a solvent and removing the solvent from the suspension or solution by distillation under reduced pressure to obtain a powder, and (ii) reacting the glycerophosphatidylcholine of the formula (II) present in the powder with an acid anhydride represented by the formula $$(RCO)_2O \qquad (III)$$

wherein R is as defined above or an acid halide represented by the formula $$RCOX \qquad (IV)$$

wherein R is as defined above and X represents halogen atom in a solvent and in the presence of tri($C_1$–$C_4$alkyl)amine or a pyridine derivative represented by the formula

wherein $R_1$ represents straight- or branched-chain alkyl group having 1 to 4 carbon atoms or two $R_1$ groups, when taken together with the nitrogen to which they are attached, form pyrrolidino group, and $R_2$ represents alkyl group having 1 to 4 carbon atoms or hydrogen atom, the amount of the compound of the formula (III) or (IV) used being 1 to 20 moles per mole of the glycerophosphatidylcholine of the formula (II) and the amount of the pyridine derivative of the formula (V) or tri($C_1$–$C_4$alkyl)amine used being 0.01 to 10 moles per mole of the glycerophosphatidylcholine of the formula (II).

8. A process as defined in claim 7 wherein R is straight- or branched-chain saturated aliphatic hydrocarbon group having 1 to 30 carbon atoms or straight- or branched-chain unsaturated aliphatic hydrocarbon group having 2 to 30 carbon atoms and 1 to 6 double bonds and/or 1 to 3 triple bonds.

9. A process as defined in claim 7 wherein the porous mineral material is zeolite, talc, terra abla, silica, alumina, kaolin, diatomaceous earth or montmorillonite.

10. A process as defined in claim 7 wherein the inorganic neutral salt is a salt of a strong acid and a strong base.

11. A process as defined in claim 7 wherein the inorganic neutral salt is magnesium sulfate, sodium sulfate, sodium chloride, calcium chloride or barium chloride.

12. A process as defined in claim 7 wherein the carrier is in the form of particles not greater than 250 μm in particle size.

13. A process as defined in claim 7 wherein the solvent used in the step (i) is water or saturated aliphatic monohydric alcohol having 1 to 3 carbon atoms.

14. A process as defined in claim 7 wherein the solvent used in the step (ii) is halogenated hydrocarbon having 1 to 2 carbon atoms; aromatic hydrocarbon; saturated aliphatic hydrocabon having 5 to 10 carbon atoms; ester of fatty acid having 2 3 carbon atoms and saturated aliphatic monohydric alcohol having 1 to 3 carbon atoms; or ether.

15. A process as defined in claim 7 wherein the pyridine derivative of the formula (V) is N,N-dimethyl-4-aminopyridine, N,N-dimethyl-4-amino-2-methylpyridine, N,N-diethyl-4-aminopyridine, N,N-dibutyl-4-amino-3-ethylpyridine, 4-pyrrolidinopyridine, 4-pyrrolidino-2-isopropylpyridine or 4-pyrrolidine-3-butylpyridine.

* * * * *